US006753461B2

(12) United States Patent
Taji et al.

(10) Patent No.: US 6,753,461 B2
(45) Date of Patent: Jun. 22, 2004

(54) METHOD FOR INCREASING STRESS-RESISTANCE TO A PLANT

(75) Inventors: Teruaki Taji, Ibaraki (JP); Kazuo Shinozaki, Ibaraki (JP); Chieko Ohsumi, Kanagawa (JP)

(73) Assignees: Ajinomoto Co., Inc., Tokyo (JP); Riken, Wako (JP)

( * ) Notice: Subject to any disclaimer, the term of this patent is extended or adjusted under 35 U.S.C. 154(b) by 0 days.

(21) Appl. No.: 09/810,506

(22) Filed: Mar. 19, 2001

(65) Prior Publication Data

US 2002/0194644 A1 Dec. 19, 2002

(30) Foreign Application Priority Data

Mar. 14, 2001 (JP) ....................................... 2001-072650

(51) Int. Cl.[7] ................................................ C12N 15/82

(52) U.S. Cl. ........................................ 800/289; 435/468

(58) Field of Search .............................. 435/468, 320.1, 435/419; 800/289, 298

(56) References Cited

PUBLICATIONS

Bachmann et al, "Metabolism of the Raffinose Family Oligosaccharides in Leaves of *Ajuga retans L.*", 1994, Plant Physiol. vol. 105, pp. 1335–1345.*

* cited by examiner

*Primary Examiner*—Phuong T. Bui
*Assistant Examiner*—Cynthia Collins
(74) *Attorney, Agent, or Firm*—Oblon, Spivak, McClelland, Maier & Neustadt, P.C.

(57) ABSTRACT

The present invention enables production of a plant resistant to environmental stresses including drought and high salt concentration. The invention increases stress resistance to a plant by increasing galactinol content in the plant.

8 Claims, 7 Drawing Sheets

ENZYMATIC ACTIVITY OF GST-AtGo1S PROTEIN

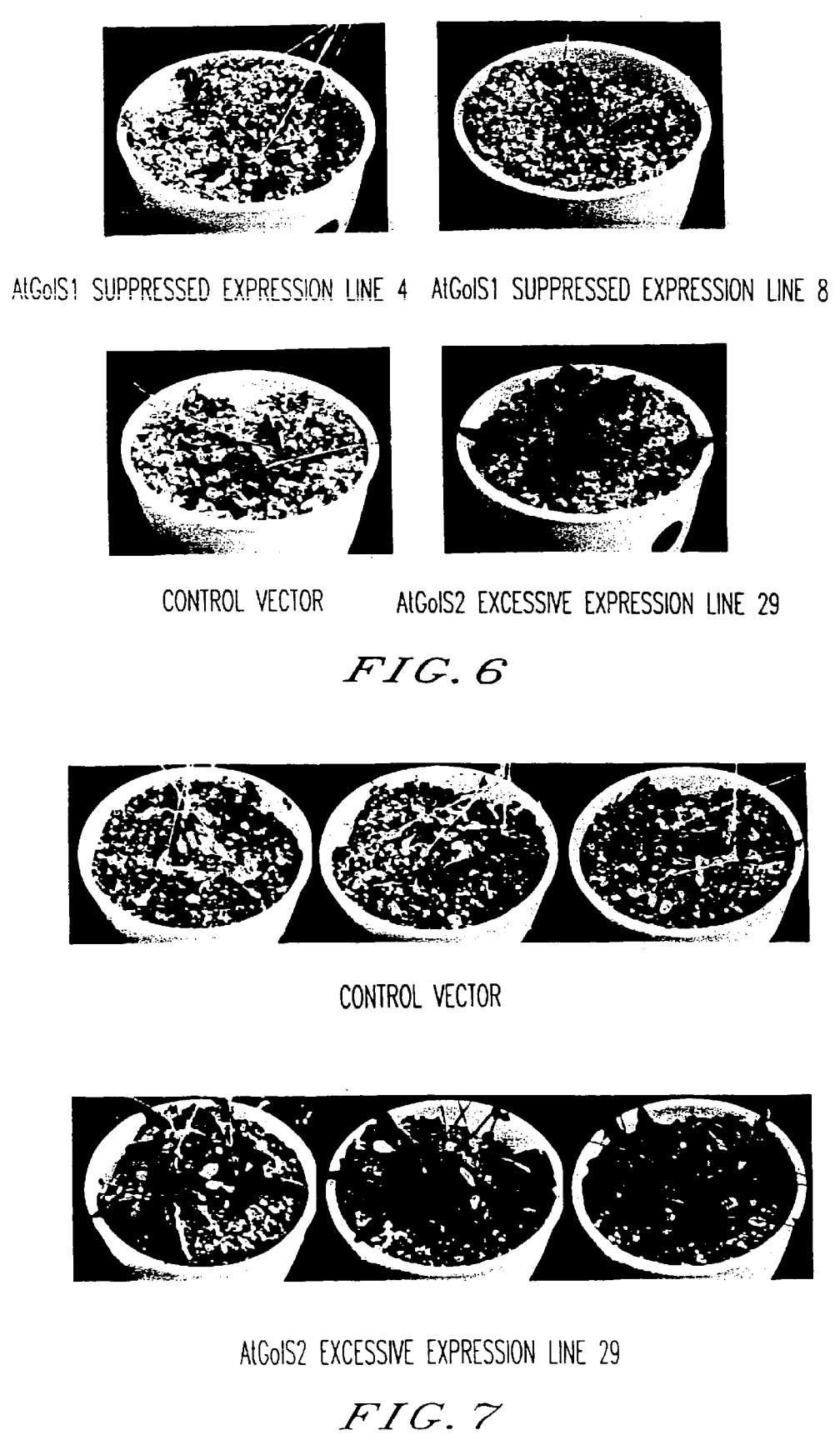

AtGolS1 SUPPRESSED EXPRESSION LINE 4 AtGolS1 SUPPRESSED EXPRESSION LINE 8

CONTROL VECTOR AtGolS2 EXCESSIVE EXPRESSION LINE 29

*FIG. 6*

CONTROL VECTOR

AtGolS2 EXCESSIVE EXPRESSION LINE 29

*FIG. 7*

SEQUENCE LISTING

```
<160> NUMBER OF SEQ ID NOS: 15

<210> SEQ ID NO 1
<211> LENGTH: 344
<212> TYPE: PRT
<213> ORGANISM: Arabidopsis thaliana

<400> SEQUENCE: 1

Met Ala Pro Gly Leu Thr Gln Thr Ala Asp Ala Met Ser Thr Val Thr
1               5                   10                  15

Ile Thr Lys Pro Ser Leu Pro Ser Val Gln Asp Ser Asp Arg Ala Tyr
            20                  25                  30

Val Thr Phe Leu Ala Gly Asn Gly Asp Tyr Val Lys Gly Val Val Gly
        35                  40                  45

Leu Ala Lys Gly Leu Arg Lys Val Lys Ser Ala Tyr Pro Leu Val Val
    50                  55                  60

Ala Met Leu Pro Asp Val Pro Glu Glu His Arg Arg Ile Leu Val Asp
65                  70                  75                  80

Gln Gly Cys Ile Val Arg Glu Ile Glu Pro Val Tyr Pro Pro Glu Asn
                85                  90                  95

Gln Thr Gln Phe Ala Met Ala Tyr Tyr Val Ile Asn Tyr Ser Lys Leu
            100                 105                 110

Arg Ile Trp Lys Phe Val Glu Tyr Ser Lys Met Ile Tyr Leu Asp Gly
        115                 120                 125

Asp Ile Gln Val Tyr Glu Asn Ile Asp His Leu Phe Asp Leu Pro Asp
    130                 135                 140

Gly Tyr Leu Tyr Ala Val Met Asp Cys Phe Cys Glu Lys Thr Trp Ser
145                 150                 155                 160

His Thr Pro Gln Tyr Lys Ile Arg Tyr Cys Gln Gln Cys Pro Asp Lys
                165                 170                 175

Val Gln Trp Pro Lys Ala Glu Leu Gly Glu Pro Pro Ala Leu Tyr Phe
            180                 185                 190

Asn Ala Gly Met Phe Leu Tyr Glu Pro Asn Leu Glu Thr Tyr Glu Asp
        195                 200                 205

Leu Leu Arg Thr Leu Lys Ile Thr Pro Pro Thr Pro Phe Ala Glu Gln
    210                 215                 220

Asp Phe Leu Asn Met Tyr Phe Lys Lys Ile Tyr Lys Pro Ile Pro Leu
225                 230                 235                 240

Val Tyr Asn Leu Val Leu Ala Met Leu Trp Arg His Pro Glu Asn Val
                245                 250                 255

Glu Leu Gly Lys Val Lys Val Val His Tyr Cys Ala Ala Gly Ser Lys
            260                 265                 270

Pro Trp Arg Tyr Thr Gly Lys Glu Ala Asn Met Glu Arg Glu Asp Ile
        275                 280                 285

Lys Met Leu Val Lys Lys Trp Trp Asp Ile Tyr Asp Asp Glu Ser Leu
    290                 295                 300

Asp Tyr Lys Lys Pro Val Thr Val Val Asp Thr Glu Val Asp Leu Val
305                 310                 315                 320

Asn Leu Lys Pro Phe Ile Thr Ala Leu Thr Glu Ala Gly Arg Leu Asn
                325                 330                 335
```

-continued

```
Tyr Val Thr Ala Pro Ser Ala Ala
            340


<210> SEQ ID NO 2
<211> LENGTH: 335
<212> TYPE: PRT
<213> ORGANISM: Arabidopsis thaliana

<400> SEQUENCE: 2

Met Ala Pro Glu Ile Asn Thr Lys Leu Thr Val Pro Val His Ser Ala
1               5                   10                  15

Thr Gly Gly Glu Lys Arg Ala Tyr Val Thr Phe Leu Ala Gly Thr Gly
            20                  25                  30

Asp Tyr Val Lys Gly Val Val Gly Leu Ala Lys Gly Leu Arg Lys Ala
        35                  40                  45

Lys Ser Lys Tyr Pro Leu Val Val Ala Val Leu Pro Asp Val Pro Glu
    50                  55                  60

Asp His Arg Lys Gln Leu Val Asp Gln Gly Cys Val Val Lys Glu Ile
65                  70                  75                  80

Glu Pro Val Tyr Pro Pro Glu Asn Gln Thr Glu Phe Ala Met Ala Tyr
                85                  90                  95

Tyr Val Ile Asn Tyr Ser Lys Leu Arg Ile Trp Glu Phe Val Glu Tyr
            100                 105                 110

Asn Lys Met Ile Tyr Leu Asp Gly Asp Ile Gln Val Phe Asp Asn Ile
        115                 120                 125

Asp His Leu Phe Asp Leu Pro Asn Gly Gln Phe Tyr Ala Val Met Asp
    130                 135                 140

Cys Phe Cys Glu Lys Thr Trp Ser His Ser Pro Gln Tyr Lys Ile Gly
145                 150                 155                 160

Tyr Cys Gln Gln Cys Pro Asp Lys Val Thr Trp Pro Glu Ala Lys Leu
                165                 170                 175

Gly Pro Lys Pro Pro Leu Tyr Phe Asn Ala Gly Met Phe Val Tyr Glu
            180                 185                 190

Pro Asn Leu Ser Thr Tyr His Asn Leu Leu Glu Thr Val Lys Ile Val
        195                 200                 205

Pro Pro Thr Leu Phe Ala Glu Gln Asp Phe Leu Asn Met Tyr Phe Lys
    210                 215                 220

Asp Ile Tyr Lys Pro Ile Pro Pro Val Tyr Asn Leu Val Leu Ala Met
225                 230                 235                 240

Leu Trp Arg His Pro Glu Asn Ile Glu Leu Asp Gln Val Lys Val Val
                245                 250                 255

His Tyr Cys Ala Ala Gly Ala Lys Pro Trp Arg Phe Thr Gly Glu Glu
            260                 265                 270

Glu Asn Met Asp Arg Glu Asp Ile Lys Met Leu Val Lys Lys Trp Trp
        275                 280                 285

Asp Ile Tyr Asn Asp Glu Ser Leu Asp Tyr Lys Asn Val Val Ile Gly
    290                 295                 300

Asp Ser His Lys Lys Gln Gln Thr Leu Gln Gln Phe Ile Glu Ala Leu
305                 310                 315                 320

Ser Glu Ala Gly Ala Leu Gln Tyr Val Lys Ala Pro Ser Ala Ala
                325                 330                 335


<210> SEQ ID NO 3
<211> LENGTH: 1064
<212> TYPE: DNA
```

-continued

<213> ORGANISM: Arabidopsis thaliana

<400> SEQUENCE: 3

```
atggctccgg ggcttactca aaccgctgat gctatgtcca ccgtgacgat aacaaaaccg      60
tcactgccat cagtccaaga cagcgatcga gcttacgtga cgtttcttgc tggaaacggt     120
gattacgtga aaggagtcgt tggtttagcc aaagggttaa ggaaagtcaa atcggcttat     180
ccactcgtag tagcgatgtt acccgacgtc ccggaggaac accgtcgtat acttgtggat     240
caaggatgca tcgtccgtga aatcgaaccc gtttacccac ccgagaacca aactcagttc     300
gccatggctt attacgtcat caactactct aaactccgta tctggaagtt tgtggagtat     360
agtaaaatga tatatttaga tggagacatt caagtttacg aaaacatcga tcacttgttt     420
gacctaccag atggctattt gtacgcggtg atggattgtt tctgtgagaa aacatggagt     480
cacacgccgc aatacaagat cagatattgc caacaatgcc ccgacaaagt ccagtggcca     540
aaagcggagc ttggagagcc accggctctt tacttcaacg ccggaatgtt cttgtacgag     600
cctaacctcg agacttacga ggatctacta cgaacactta aaatcactcc tccgactcct     660
ttcgctgaac aggatttttt gaacatgtac tttaagaaaa tctacaagcc gattccttta     720
gtgtacaatc tcgtccttgc gatgttatgg cgtcacccag aaaatgtaga gcttggaaaa     780
gtcaaggtgg ttcactactg tgcagcgggt tcgaagccgt ggagatacac agggaaagaa     840
gcgaacatgg agagggaaga tataaaaatg ttagtgaaaa aatggtggga catttacgac     900
gacgaatcct tggattacaa gaaacctgtt accgttgtgg acacagaggt cgatctcgtg     960
aatctgaagc cgttcatcac cgctcttact gaagctggcc ggctcaacta cgtgaccgca    1020
ccgtccgctg cttgaatgtt gccaggagtt aaaattgtcg gtgg                     1064
```

<210> SEQ ID NO 4
<211> LENGTH: 29
<212> TYPE: DNA
<213> ORGANISM: Artificial Sequence
<220> FEATURE:
<223> OTHER INFORMATION: synthetic DNA

<400> SEQUENCE: 4

```
caaggatccg cagatcacgt gctaatcac                                        29
```

<210> SEQ ID NO 5
<211> LENGTH: 29
<212> TYPE: DNA
<213> ORGANISM: Artificial Sequence
<220> FEATURE:
<223> OTHER INFORMATION: synthetic DNA

<400> SEQUENCE: 5

```
caaggatccc ctggcaatca agcagcgga                                        29
```

<210> SEQ ID NO 6
<211> LENGTH: 22
<212> TYPE: DNA
<213> ORGANISM: Artificial Sequence
<220> FEATURE:
<223> OTHER INFORMATION: synthetic DNA

<400> SEQUENCE: 6

```
cgccacagta caagatcggt ta                                               22
```

<210> SEQ ID NO 7
<211> LENGTH: 20

-continued

<212> TYPE: DNA
<213> ORGANISM: Artificial Sequence
<220> FEATURE:
<223> OTHER INFORMATION: synthetic DNA

<400> SEQUENCE: 7
catgaagagg cgtatgcagc 20

<210> SEQ ID NO 8
<211> LENGTH: 20
<212> TYPE: DNA
<213> ORGANISM: Artificial Sequence
<220> FEATURE:
<223> OTHER INFORMATION: synthetic DNA

<400> SEQUENCE: 8
ctttctcgga caagatggca 20

<210> SEQ ID NO 9
<211> LENGTH: 20
<212> TYPE: DNA
<213> ORGANISM: Artificial Sequence
<220> FEATURE:
<223> OTHER INFORMATION: synthetic DNA

<400> SEQUENCE: 9
gtgttgacaa gaacctcgct 20

<210> SEQ ID NO 10
<211> LENGTH: 32
<212> TYPE: DNA
<213> ORGANISM: Artificial Sequence
<220> FEATURE:
<223> OTHER INFORMATION: synthetic DNA

<400> SEQUENCE: 10
cgcggatcca tggctccggg gcttactcaa ac 32

<210> SEQ ID NO 11
<211> LENGTH: 32
<212> TYPE: DNA
<213> ORGANISM: Artificial Sequence
<220> FEATURE:
<223> OTHER INFORMATION: synthetic DNA

<400> SEQUENCE: 11
cgcggatccc caccgacaat tttaactcct gg 32

<210> SEQ ID NO 12
<211> LENGTH: 30
<212> TYPE: DNA
<213> ORGANISM: Artificial Sequence
<220> FEATURE:
<223> OTHER INFORMATION: synthetic DNA

<400> SEQUENCE: 12
cgcggatcca tggcacctga gatcaatacc 30

<210> SEQ ID NO 13
<211> LENGTH: 30
<212> TYPE: DNA
<213> ORGANISM: Artificial Sequence
<220> FEATURE:
<223> OTHER INFORMATION: synthetic DNA

<400> SEQUENCE: 13

-continued

```
cgcggatccg aggcgtatgc agcaacgagc                                    30


<210> SEQ ID NO 14
<211> LENGTH: 36
<212> TYPE: DNA
<213> ORGANISM: Artificial Sequence
<220> FEATURE:
<223> OTHER INFORMATION: synthetic DNA

<400> SEQUENCE: 14

cgcggatcca tggcacctga gatgaacaac aagttg                             36


<210> SEQ ID NO 15
<211> LENGTH: 33
<212> TYPE: DNA
<213> ORGANISM: Artificial Sequence
<220> FEATURE:
<223> OTHER INFORMATION: synthetic DNA

<400> SEQUENCE: 15

cgcggatccc tggtgttgac aagaacctcg ctc                                33
```

METHOD FOR INCREASING STRESS-RESISTANCE TO A PLANT

FIELD OF THE INVENTION

The present invention relates to a method for increasing stress-resistance to a plant. That is, the method can impart a plant with stress-resistance including good drought resistance and/or resistance to high salt concentration.

BACKGROUND OF THE INVENTION

The importance of agricultural use of the arid zone, which occupies approximately one third of the land on the earth, is increasingly recognized as a measure against predicted serious food scarcity. This problem should be addressed as soon as possible. Now the proportion of dry and semi-dry soil inappropriate for agriculture is increasing year after year due to saline accumulation, and drying or heat caused by, for example, excessive irrigation water (Manabu Sekiya, et al., Chemical Regulation in Plant Vol. 25, No. 2, 149–162, 1990). One of the solutions to this problem is a method in which resistance mechanisms against these environmental stresses are elucidated and a plant resistant to these stresses is produced.

Plants are immobile. Thus they must be tough enough to endure their environmental changes in order to keep differentiating and growing. Therefore, it is thought that plants have acquired through the course of evolution a response mechanism to respond promptly and adapt to environmental changes. Of the environmental factors surrounding plants, drought and saline accumulation are important factors concerning life or death of terrestrial plants. These factors largely affect plant growth. Plant growth is inhibited by drought stress. That is, it causes decreased turgor pressure and affects various physiological pathways (Shinozaki and Yamaguchi-Shinozaki, Plant Physiol. 115: 327–334, 1997).

In plants, it has been shown that various response mechanisms act against these stresses at an individual level, tissue level, and cellular level, and in addition through molecular biological research at a gene expression level. In other words, in various plants, a response mechanism at a gene expression level, including the presence of many stress-inducible genes whose mRNA amount increases upon drying and treatment with salt, has been elucidated. Plants are thought to acquire resistance from any one of the products of the stress-inducible gene group.

Abscisic acid (ABA), one of a plant's hormones, is deeply involved in expression of the stress-inducible gene group. When a plant is exposed to a stress, such as drought stress, signal-transduction occurs via ABA dependent pathway and ABA independent pathway, and the signal-transduction regulates the expression of the stress-inducible gene group. The gene group includes those involved in synthesis of compatible solutes, such as proline and glycine betaine. Proline and glycine betaine have been well studied. It is known that a transgenic plant, in which proline or glycine betaine is excessively accumulated by engineering the synthetic or decomposition system, shows resistance to NaCl or low temperature stress.

On the other hands in the biosynthetic pathway for RF0, galactinol is first synthesized by galactinol synthetase. Next, raffinose is synthesized by raffinose synthetase using the galactinol and sucrose as substrates, and finally stachyose is synthesized by stachyose synthetase using the galactinol and raffinose as substrates, as shown in FIG. 10. A generic name for raffinose and stachyose is RF0. So far, every report concerning RF0 suggests that raffinose and stachyose play an important role in drought resistance of seeds (Blackman S. A. et al. Plant Physiol. 100: 225–230, 1992, Ooms J. J. J. et al. Plant Physiol. 102: 1185–1192, 1993).

There is no report concerning functions or roles of RF0 in a plant body other than those in a seed. A seed and a plant body may share an overlapping mechanism for acquiring drought resistance, or they may have totally different mechanisms.

For example, it is known that stresses, such as drought conditions, cause a plant to close stomata by accumulation of ABA as described above to suppress transpiration, thereby preventing water loss. Actually, ABA-deficient Arabidopsis mutants aba1 having an altered ABA synthetic system wither easily such that they cannot grow at a normal humidity. However, ABA-deficient mutant seeds can bud even under completely drought conditions. In other words, no decrease in drought resistance is found in ABA-deficient mutant seeds (Koornneef, M et al., Physiol. Plant. 61: 377–383, 1984, Duckham, S. C. et al., Plant Cell and Environ. 14: 601–606, 1991, Rock, C. D. and Zeevaart, J. A. D., Proc. Natl. Acad. Sci. 88: 7496–7499, 1991).

Moreover, seeds of ABA insusceptible Arabidopsis mutant abi3 are known to lack drought resistance. Under complete drought conditions, the seeds lose their budding ability. However, the seeds disseminated before progression of drying can bud, and no phenotype that withers like aba1 is observed (Nambara, E., et al, Polant J. 2: 435–441, 1992, Kriz, A. R., et al, Plant Physiol. 92: 538–542, 1990, Parcy, F., et al, Plant Cell 6: 1567–1582). In conclusion, ABI3 possesses a mechanism to acquire drought resistance, which functions only in its seed, and whose action is far greater than of ABA.

As described above, there is a great difference between a seed and a plant body in respect of drought resistance acquisition mechanism. Whether RF0, which is suggested to be important in drought resistance of a seed, plays a role in drought resistance of a plant body remains unknown and cannot even be predicted.

SUMMARY OF THE INVENTION

Accordingly, an object of the present invention is to provide a method for increasing stress resistance to a plant, which enables production of a plant having resistance against environmental stresses including drought and/or high salt concentration.

After thorough study, the inventors have completed the invention by finding that an increased content of galactinol in a plant body can provide the plant with stress resistance.

The present invention encompasses the followings:

(1) a method for increasing stress resistance to a plant wherein a galactinol synthetase gene is introduced into the plant body.

(2) The method for increasing stress resistance to a plant according to (1) wherein the galactinol synthetase gene is the following gene (a) or (b):

(a) a gene encoding a protein comprising an amino acid sequence represented by SEQ ID NO: 1, (b) a gene encoding a protein comprising an amino acid sequence differing from the amino acid sequence of SEQ ID NO: 1 by deletion, substitution or addition of at least one or more amino acids, and having galactinol synthetic activity.

(3) The method for increasing stress resistance to a plant according to (1) wherein the galactinol synthetase gene is the following gene (c) or (d):

(c) a gene encoding a protein comprising an amino acid sequence represented by SEQ ID NO: 2, (d) a gene encoding a protein comprising an amino acid sequence differing from the amino acid sequence of SEQ ID NO: 2 by deletion, substitution or addition of at least one or more amino acids, and having galactinol synthetic activity.

(4) The method for increasing stress resistance to a plant according to (1) wherein galactinol content in the plant body is increased.

(5) The method for increasing stress resistance to a plant according (1) wherein galactinol synthetic activity in the plant body is improved.

(6) A method for increasing stress resistance to a plant which comprises increasing galactinol content in the plant body.

(7) A method for increasing stress resistance to a plant which improving galactinol synthetic activity in the plant body.

(8) A method for increasing stress resistance to a plant which excessively expressing the following protein (e) or (f) in the plant body:

(e) a protein comprising an amino acid sequence represented by SEQ ID NO: 1, (f) a protein comprising an amino acid sequence differing from the amino acid sequence of SEQ ID NO: 1 by deletion, substitution or addition of at least one or more amino acids, and having galactinol synthetic activity.

(9) A method for increasing stress resistance to a plant which excessively expressing the following protein (g) or (h) in the plant body:

(g) a protein comprising an amino acid sequence represented by SEQ ID NO: 2, (h) a protein comprising an amino acid sequence differing from the amino acid sequence of SEQ ID NO: 2 by deletion, substitution or addition of at least one or more amino acids, and having galactinol synthetic activity.

BRIEF DESCRIPTION OF THE DRAWINGS

FIG. 6 contains photographs showing how transgenic plants grew under drought stress.

FIG. 7 contains photographs showing how transgenic plants grew under drought stress followed by reabsorption of water.

DETAILED DESCRIPTION OF THE INVENTION

Figure 1:
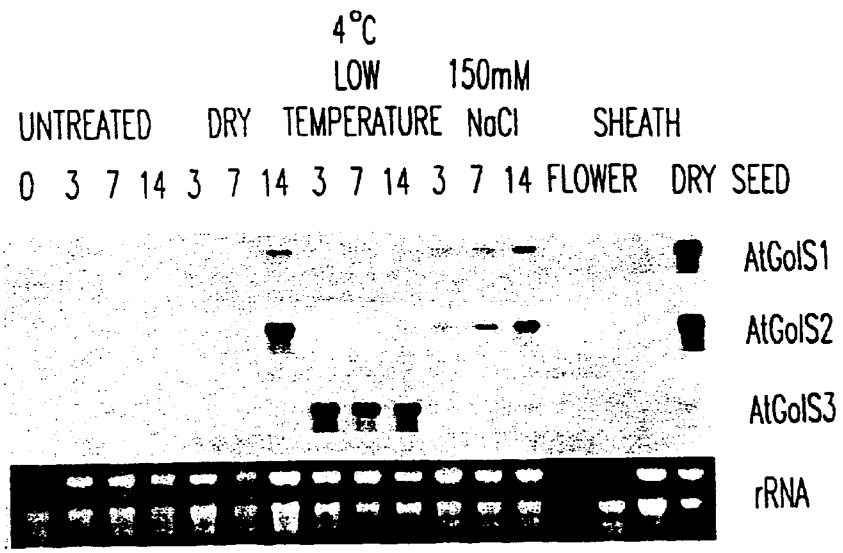
FIG. 1 shows a photograph of electrophoresis by which expression of AtGo1S1 to 3 in Arabidopsis plants that grew on soil and were exposed to various stresses was confirmed.

More detailed description concerning the method for increasing stress resistance to a plant according to the present invention will be given as follows.

The method for increasing stress resistance to a plant body according to this invention comprises the steps of introducing a gene (called galactinol synthetase gene) that encodes galactinol synthetase into a plant so as to increase stress resistance to the plant. Examples of plants include, but are not limited to, Arabidopsis, Glycine, Vicia, rape-seed, Helianthus, Gossypium, sugar beat, Oryza, Saccharum, corn and Sorghum.

Any galactinol synthetase gene may be used herein so far as it encodes a protein having galactinol synthetase activity. Galactinol synthetase activity is activity to synthesize galactinol using UDP-galactose and myo-inositol as substrates. For example, a galactinol synthesis reaction is conducted by adding fractions, which contain galactinol synthetase extracted from a plant body, to a reaction solution, which contains UDP-galactose and myo-inositol. Then galactinol synthesized in the reaction solution is determined so that galactinol synthetic activity can be evaluated. More specifically, activity can be measured according to the methods described in Liu, J. J. et al's report (Plant Physiol. 109: 505–511, 1995). That is, 0.017 mg of protein to be measured is added to a reaction buffer (50 mM Hepes-Na, 2 mM DTT, pH7.0) containing 4 mM $MnCl_2$, followed by incubation at 30° C. for 15 minutes. Next, 4 mM UDP-galactose, 20 mM myo-inositol and 0.16 mg BSA are added to the resulting solution, followed by another incubation at 30° C. for 30 minutes in a total 1 ml of a system for galactinol synthesis reaction to proceed. Then galactinol in the reaction solution is determined. In addition, the galactinol synthesis reaction can be stopped by addition of 2 ml of cold 100% EtOH following reaction.

Galactinol synthetase gene can also be prepared from a plant body. Any plant which synthesizes galactinol may be used. Such plants include Arabidopsis, Vicia, rape-seed, Helianthus, Gossypium, and sugar beat.

Nucleotide sequence information of the galactinol synthetase gene can be obtained by searching genes having homology with galactinol synthetase genes derived from Arabidopsis based on a database, such as GenBank. Examples of homology analytical programs may include GENETIX-MAC (Gene information processing software, Software Development) which adopts the Lipman-Pearson method and programs available on the Internet. Nucleotide sequences thus obtained by the program as described above may or may not contain the full length gene. Even when the sequence does not contain the full length sequence, a full length sequence can be easily obtained by 5' RACE and 3' RACE using RNA extracted from a target plant tissue as a template and a primer corresponding to a site sharing high homology with a galactinol synthetase gene derived from Arabidopsis. The resultant full length sequence is integrated into an appropriate expression vector, which is provided by a kit, such as Soluble Protein Expression system (INVITROGEN), Tight Control Expression System (INVITROGEN), or QIAexpress System (QIAGEN) for gene expression. Subsequently, galactinol synthetase activity is measured as described above, and then clones having activity are screened. Detailed description for expressing genes are given in Plant Molecular Biology, A Laboratory Manual (Melody S. Clark (Ed.), Springer) and the like.

Moreover, a galactinol synthetase gene can be obtained by preparing a cDNA library from poly(A)+ RNA isolated from a plant body, such as Arabidopsis, and by screening the cDNA library with hybridization.

Probes used for hybridization can be obtained by PCR (Polymerase Chain Reaction) amplification using oligonucleotides, which are synthesized based on a partial amino acid sequence of galactinol synthetase, as primers.

Now, a method to obtain a galactinol synthetase gene from poly(A)$^+$ RNA will be described in detail. Any site for extracting poly(A)$^+$ RNA maybe used so far as a galactinol synthetase gene expresses therefrom. A method to extract total RNA is not limited, and any method which is effective in obtaining less-damaged RNA may be employed. Examples of such a method include the phenol/SDS method, guanidine isothiocyanate/cesium chloride method, and any known method. Then, poly(A)$^+$ RNA can be isolated from thus obtained total RNA using oligo(dT) carriers. In addition, any kit (MPG Direct mRNA Purification Kit, CPG, INC. and the like), by which poly(A)$^+$ RNA can be obtained without extracting total RNA, may be used.

To construct a cDNA library, first, a single-stranded cDNA is synthesized using poly(A)$^+$ RNA as a template and oligo(dT) primer, random primer and the like, and reverse transcriptase. Next, a double-stranded cDNA is synthesized by Gubler and Hoffman's method, Okayama-Berg method (Molecular Cloning 2$^{nd}$ edition, Cold Spring Harbor press, 1989) and the like. In case of a low expression amount of a galactinol synthetase gene, cDNA may be amplified by PCR using a kit for constructing a cDNA library (Capfinder PCR cDNA Library Construction Kit (CLONTECH). Thus synthesized cDNA can be cloned into cloning vectors including phage vectors and plasmids by blunt-ending, addition of a linker, and addition of restriction enzyme sites by PCR.

DNA fragments used as probes for screening a cDNA library can be obtained by PCR. For example, a database containing genome nucleotide sequences of a plant for extraction, such as Arabidopsis, is searched for a target gene homolog, using nucleotide sequence information of a known galactinol synthetase gene homolog in a plant, such as Oryza. Accordingly, a galactinol synthetase gene homolog is identified in the plant for extraction so that a primer for PCR can be designed.

Probes for hybridization can be prepared by PCR using the primers designed and synthesized as described above and genome DNA. In addition, a probe can also be prepared by the so-called RACE method (Rapid Amplification of cDNA End: PCR PROTOCOLS A Guide to Methods and Applications, ACADEMIC press INC. p.28–38). Examples of labels for probes include radioisotope, biotin, and other various substances. Preferably, labeling is performed by the random priming method. Further, screening is not only performed by hybridization, but also by PCR. Furthermore, a combination of hybridization and PCR may be employed. When no genome information of a plant for extraction can be obtained, screening can be performed using a probe prepared based on the nucleotide sequence information of galactinol synthetase homolog in a heteroplant.

Other than the above methods, the following methods can be used for cloning of a galactinol synthetase gene.

(1) Galactinol synthetase is isolated and purified from a plant, and then a total nucleotide sequence is chemically synthesized based on the amino acid sequence determined.

(2) Chromosomal DNA is prepared from a plant body, chromosomal DNA library is constructed using plasmid vectors and the like. Then a galactinol synthetase gene is obtained from the library by hybridization or PCR. Here, a galactinol synthetase gene derived from a chromosome is predicted to have introns in the coding region. Even if DNA is divided by such introns, the DNA is included in the DNAs of this invention so far as it encodes galactinol synthetase.

(3) Poly(A)$^+$ RNA is fractioned by molecular weight and the like, and the fraction is subjected to in vitro translation system using wheat germ or rabbit blood reticulocytes. Then fractions, in which mRNA encoding a polypeptide having galactinol synthetase activity, are determined, thereby constructing and obtaining a cDNA fragment of interest.

(4) A galactinol synthetase antibody is prepared, and then cDNA library is integrated into a protein expression vector. Next, an appropriate host is infected with the vector to express the protein encoded by the cDNA. Using the antibody, cDNA of interest is screened.

(5) An appropriate primer is synthesized from an amino acid sequence of a peptide fragment, followed by amplification of a sequence containing the terminal by the RACE method. Then the amplified sequence is cloned.

For expression of a galactinol synthetase gene, DNA of a region encoding the enzyme may be integrated into a variety of expression vectors. Detailed information on this matter is described in e.g., Plant Molecular Biology—A Laboratory Manual (M. S. Clark (eds.), Springer). Commercial expression vectors may be used herein. Expression can be confirmed by measuring activity according to the method described in this specification.

Examples of galactinol synthetase genes include a gene encoding a protein comprising an amino acid sequence of SEQ ID NO: 1, or a gene encoding a protein comprising an amino acid sequence differing from that of SEQ ID NO: 1 by deletion, substitution, or addition of at least one or more amino acids and having galactinol synthetic activity.

Moreover, examples of a galactinol synthetase gene include a gene encoding a protein comprising an amino acid sequence of SEQ ID NO: 2, or a gene encoding a protein comprising an amino acid sequence differing from that of SEQ ID NO: 2 by deletion, substitution, or addition of at least one or more amino acids and having galactinol synthetic activity. In addition, an example of a galactinol synthetase gene is a gene of SEQ ID NO: 3.

A galactinol synthetase gene may be a gene encoding a galactinol synthetase protein comprising an amino acid sequence differing from that of SEQ ID NO:1 or 2 by substitution, deletion, insertion, addition, or inversion of one or more amino acids at one or more positions so far as the protein have intact activity to synthesize galactinol from UDP-galactose and myo-inositol. A galactinol synthetase gene may be any gene which encodes a protein having galactinol synthetase activity. "Galactinol synthetase activity" is activity to synthesize galactinol using UDP-galactose and myo-inositol as substrates. That is, a fraction containing galactinol synthetase extracted from a plant body is added to a reaction solution having UDP-galactose and myo-inositol to proceed galactinol synthetic reaction. Then galactinol synthetic activity can be evaluated by determining galactinol synthesized in the reaction solution. More specifically, activity can be measured according to the methods described in Liu, J. J. et al., Plant Physiol. 109: 505–511, 1995. For example, 0.017 mg of protein to be measured is added to a reaction buffer (50 mM Hepes-Na, 2 mM DTT, pH7.0) containing 4 mM $MnCl_2$, and then incubated at 30° C. for 15 minutes. Following incubation, 4 mM UDP-galactose, 20 mM myo-inositol and 0.16 mg of BSA are added to the solution, followed by incubation in a total of 1 ml system at 30° C. for 30 minutes for galactinol synthetic reaction to proceed. Finally, galactinol in the reaction solution is determined. In addition, the galactinol synthetic reaction can be stopped by the addition of 2 ml of cold 100% EtOH following reaction. A protein considered to possess galactinol sysnthetase activity should have activity of 30% or more, preferably 60% or more, more preferably 80% or more, most preferably 90% or more of that of galactinol synthetase represented by SEQ ID NO: 1 or 2.

A method, known among persons in the art, for preparing a galactinol synthetase gene encoding a protein consisting of an altered amino acid sequence is, for example in vitro mutagenesis by PCR (Tsuyoshi Izawa, in vitro mutagenesis by PCR, pp 151–158, ed., Isao Shimamoto, Takuji Sasaki, Cell Engineering, special number, Plant Cell Engineering Series 7, New PCR Experimental Protocol, Shu-jun sha). Number of the amino acid for artificial alteration is 200 or less, preferably 100 or less, more preferably, 50 or less, more preferably 10 or less. In nature, mutation in a nucleotide sequence may cause mutation in an amino acid sequence of a protein. Such a mutated galactinol synthetase gene encoding a protein consisting of an amino acid sequence differing from that of a natural type galactinol synthetase gene by substitution, deletion, addition, and/or insertion of one or more amino acids may also be included in the galactinol synthetase gene of this invention, so far as it encodes a protein having galactinol synthetic activity. Moreover, mutation in a nucleotide sequence may not cause mutation in an amino acid in a protein (degenerate mutation). Such a degenerate mutant is also included in the galactinol synthetase gene of this invention.

Such a galactinol synthetase gene encoding a protein consisting of an amino acid sequence other than that of SEQ ID NO: 1 or 2 can be obtained. For example, a nucleotide sequence of galactinol synthetase gene represented by SEQ ID NO: 3 is altered by site-specific mutagenesis so that the amino acid at a specific site is substituted, deleted, inserted, or added. Furthermore, an altered galactinol synthetase gene as described above can also be obtained by known standard techniques for mutation. Example of such techniques include a method, in which galactinol synthetase gene is treated in vitro with e.g., hydroxylamine, and a method, in which bacteria involved in the genus Escherichia retaining galactinol synthetase genes are treated under UV irradiation, or with mutagens, normally used for artificial mutation, including N-methyl-N'-nitro-N-nitrosoguanidine (NTG) or nitrous acid.

Further, substitution, deletion, insertion, addition or inversion of bases as described above includes naturally occurring mutations based on plant body individual differences, inbred difference, multiplication of a gene, differences among each of organs and tissues.

A galactinol synthetase gene encoding galactinol synthetase which has an amino acid sequence differing from that of SEQ ID NO: 1 or 2 can be obtained by expression of a galactinol synthetase gene having mutation as described above, followed by examination of galactinol synthetic activity in expression products. Furthermore, a galactinol synthetase gene encoding galactinol synthetase and having an amino acid sequence differing from that of SEQ ID NO: 1 or 2 can be obtained by isolating DNA which hybridizes to a galactinol synthetase gene containing a mutation under stringent conditions and encodes a protein having galactinol synthetase activity. The term "stringent conditions" indicates a condition in which so-called specific hybrids are formed and nonspecific hybrids are not formed. It is difficult to convert precisely the stringent conditions into numeric values. For example, a condition which allows hybridization of DNAs having homology of 50% or more to each other, but allows no hybridization of DNAs having homology of less than 50%. Another example is a condition which allows hybridization at a salt concentration corresponding to normal washing conditions for Southern hybridization, which consists of 60° C., 1×SSC and 0.1% SDS, preferably, 0.1×SSC and 0.1% SDS. Genes capable of hybridizing under such conditions include those containing a stop codon inserted or losing activity due to a mutated active center. However, such a gene can be easily removed by integrating it to a commercial expression vector and measuring galactinol synthetase activity by the method as described above. A protein, which is considered to possess galactinol sysnthetase activity, should have activity of 30% or more, preferably 60% or more, more preferably 80% or more, most preferably 90% or more of that of galactinol synthetase represented by SEQ ID NO: 1 or 2.

A transgenic plant, which excessively expresses galactinol synthetase, can be obtained by introducing galactinol synthetase gene as described above into the plant body. To introduce a galactinol synthetase gene, an expression vector, to which the galactinol synthetase gene is integrated downstream of a certain promoter, is constructed. When an expression vector is constructed, the methods described in e.g., Plant Molecular Biology-A Laboratory Manual (M. S. Clark (eds.), Springer) are employed appropriately. Commercial vectors may be used. Methods of transformation are not specifically limited. Examples of transformation methods include a method for infecting with Agrobacteria (see Japanese Patent Laid Open Publication No. 2-58917), electroporation (see Japanese Patent Laid Open Publication No. 5-68575), the particle gun method (see Japanese Patent Laid Open Publication No. 5-508316). Particularly, transformation for plants belonging to the family Brassicaceae can be performed according to the method described in Plant Cell Reports (1987), 6, 321–325. Transformation for soybeans can be performed according to the methods described in Pro. Natl. Acad. Sci. USA, 86. 145 (1989), TIBTECH, 8, 145 (1990), Bio/Technology, 6, 923 (1988), Plant Physiol., 87, 671 (1988), Plant Physiol., 91, 1212 (1992), Bio/Technology, 6, 915 (1988), Plant Physol., 99, 81 (1992) and the like. Transformation for rice can be performed according to the method described in Experimental Protocol for Model Plant, Rice and *Arabidopsis thaliana* (p. 78). Expression of a galactinol synthetase gene can be confirmed by measuring activity by the method as described in this specification.

The resulting transgenic plant possesses improved stress resistance. The term "stress" indicates, for example high salt concentration and/or drought condition. The transgenic plant can suppress the amount of water absorbed by soil by suppressing the transpiration rate. Here the term "drought condition" indicates a condition under which wild type plants can grow, but growth is suppressed because of limited humidity and water supply. Further, the term "high salt concentration" is not specifically limited, but indicates a condition in which the salt content of agricultural fertilizers, acidic soil, or alkaline soil (e.g., NaCl) is high.

Improved resistance against stress including high salt concentration and/or drought conditions means that the degree of growth suppression is subdued even under conditions which suppress the growth or allow no growth of wild type plants. Examples of growth evaluation methods include, but are not limited, growth rate, plant length, weight, leaf area, flower fertility, pollen fertility, seed weight or yield, or a combination of these.

Transgenic plants may be homozygotes, or heteroprogeny plants obtained by back crossing a wild type plant with a homozygote. Moreover, stress resistance of a heterozygote may be more improved than that of a wild type plant, and stress resistance of a homozygote may be more improved than that of a heterozygote.

Galactinol content in a plant body can be increased by introducing a galactinol synthetase gene into the plant body. Galactinol is a sugar component which is synthesized by galactinol synthetase using UDP-galactose and myo-inositol as substrates. When galactinol content in a plant body is measured, first, fluid containing galactinol is extracted from a plant body. The extract can be obtained from a plant body as follows. That is, the extract is frozen with liquid nitrogen, crushed, added with 10 ml of 80% ethanol preheated to 80° C., and then boiled for 10 minutes at 90° C. Then this series of steps is repeated twice (a total of three rounds of these steps is performed).

Next, the extract is determined with HPLC (high-speed liquid chromatography). HPLC can be performed using sugar analysis system DX500 (CarboPac MA1, pulsed amperometry detector (Dionex Corporation). As described above, determination of galactinol content in an extract from a plant enables detection of an increase in galactinol content in the plant.

In this method, "increased galactinol content" indicates that a plant body to be measured contains galactinol in an amount greater than that in a wild type plant body grown under the same conditions as the transgenic plant. More specifically, it indicates that galactinol content per rosette leaf (fresh weight) is 1.1 to 50 fold, preferably 2 to 30 fold, more preferably 5 to 20 fold greater than that of an intact wild type plant. More preferably, it indicates that galactinol content (fresh weight) of a whole plant body is 1.1 to 50 fold, preferably 2 to 30 fold, more preferably 5 to 20 fold greater than that of an intact wild type plant body.

Galactionl content of a plant body can also be increased by improving galactinol synthetic activity in the plant so as to increase stress resistance to the plant. Galactinol synthetic activity can be measured according to the methods described in Liu, J. J. et al., Plant Physiol. 109: 505–511, 1995. That is, 0.017 mg of protein to be measured is added to a reaction buffer (50 mM Hepes-Na, 2 mM DTT, pH7.0) containing 4 mM $MnCl_2$, followed by incubation at 30° C. for 15 minutes. Next, 4 mM UDP-galactose, 20 mM myo-inositol and 0.16 mg BSA are added to the resulting solution, followed by another incubation at 30° C. for 30 minutes in a total 1 ml of a system for galactinol synthesis reaction to proceed. Then galactinol in the reaction solution is determined. In addition, galactinol synthesis reaction can be stopped by addition of 2 ml of cold 100% EtOH following reaction.

Moreover, "increased galactinol synthetic activity in a plant body" means that activity or specific activity per fresh weight or per leaf of a transgenic plant is improved compared to galactinol synthetase activity of a wild type plant body grown under the same conditions. More specifically it indicates that activity per fresh weight of a rosette leaf is 1.1 to 50 fold, preferably 2 to 30 fold, more preferably 5 to 20 fold greater than that of an intact wild type plant. More preferably, it indicates that activity per fresh weight of a whole plant body is 1.1 to 50 fold, preferably 2 to 30 fold, more preferably 5 to 20 fold greater than that of an intact wild type plant. However, intrinsic galactinol synthetase activity in a wild type plant cannot always be detected depending on species or habitat. In this case, "improved galactinol synthetic activity of a plant body" indicates that the plant body possesses activity to a detectable degree.

Examples of a method to increase galactinol synthetic activity in a plant body include a method, in which a galactinol synthetase gene incorporated into a vector, which allows gene expression, is introduced into a plant body; a method, in which a galactinol synthetase gene is introduced onto a plant chromosome; and a method, in which a gene encoding a transcriptional factor that enhances expression of a galactinol synthetase gene on a chromosome is introduced into a plant body.

Alternatively, screening may be performed for a mutant showing improved expression of a galactinol synthetase gene. For example, a plant having increased transcriptional activity of a raffinose synthetase gene may be screened by Northern blot analysis using a chemical mutagenesis agent, such as ethylmethane sulfonate (EMS).

In another method to increase galactnol synthetic activity, a protein is extracted from mutants obtained using a chemical mutagenesis agent, such as ethylmethane sulfonate (EMS), followed by screening by Western blot analysis or ELISA for those having large protein mass of galactinol synthetase.

All publications, patents and patent applications cited herein are incorporated into this specification by reference in their entirety.

EXAMPLE

Now a more detailed description of the present invention will be provided using examples. The technical scope of this invention is not limited by the following examples.

Example 1

1. Isolation of Galactinol Synthetase Gene

Homolog in the nucleotide sequence of Arabidopsis chromosome was searched using Blast Search (National Center for Biotechnology Information, NCBI) based on the nucleotide sequence (Takahashi, R. et al. Plant Mol. Biol., 26: 339–352) of rice galactinol synthetase gene homolog wsi76 (water stress-induced). Thus, 7 regions with high homology were found. Then Northern blot analysis was conducted for these 7 regions, thereby finding 3 regions that have expressed in response to stress. Primers for amplifying stress-responsive 3 regions were designed as follows.

```
Primer 1:
5'-CAAGGATCCGCAGATCACGTGCTAATCAC-3'  (SEQ ID NO:4)

Primer 2:
5'-CAAGGATCCCCTGGCAATCAAGCAGCGGA-3'  (SEQ ID NO:5)

Primer 3:
5'-CGCCACAGTACAAGATCGGTTA-3'         (SEQ ID NO:6)

Primer 4:
5'-CATGAAGAGGCGTATGCAGC-3'           (SEQ ID NO:7)

Primer 5:
5'-CTTTCTCGGACAAGATGGCA-3'           (SEQ ID NO:8)

Primer 6:
5'-GTGTTGACAAGAACCTCGCT-3'           (SEQ ID NO:9)
```

The DNA to be amplified by PCR using Arabidopsis chromosomal DNA as a template, and primers 1 and 2, is a DNA fragment contained in an Arabidopsis galactinol synthetase gene AtGolS1. Similarly, DNA to be amplified by PCR using primers 3 and 4 is a DNA fragment contained in an Arabidopsis galactinol synthetase gene AtGolS2. Furthermore, DNA to be amplified by PCR using primers 5 and 6 is a DNA fragment contained in an Arabidopsis galactinol synthetase gene AtGolS3.

DNA fragments amplified by each PCR were separately cloned into EcoRV sites of pBluescript II SK+ (Stratagene). A full length cDNA library (Seki et al. Plant J. 15: 707–720, 1995) prepared from Arabidopsis exposed to drying treatment was screened using plasmids, into which DNA fragments have been separately cloned, as probes. Thus nucleotide sequence of the obtained full length cDNA was determined.

2. Expression of Galactinol Synthetase Gene

First, Arabidopsis seeds (*Arabidopsis thaliana*, columbia, wt) were sowed on MS media [Murashige Skoog media (Murashige and Skoog 1962), mineral salt, 1×B5 Vitamin (Ganborg et al. 1968), 0.5% MES, 3% sucrose, pH5.7, 0.8% agar]. The media were subjected to cold treatment at 4° C. for 2 days, and then grown at 22° C. for 3 weeks.

Arabidopsis plants grown on MS plates were slowly pulled out. Agar attached to the roots was removed using a Kim wipe. These plants were then put into an empty Petri dish and subjected to drying treatment in the dish closed with a cap for 30 minutes to avoid rapid drying, thereby exposing these Arabidopsis plants to drought stress. Other Arabidopsis plants pulled out from MS plates in the same way as in the case of the drying treatment above, were placed in a 250 mM NaCl solution (ion exchange water supplemented with NaCl), which had been poured into a Petri dish so that the roots would be soaked (approximately 10 ml, leaves were not immersed in the solution as far as possible), thereby exposing these plants to high salt concentration stress. Further, instead of 250 mM NaCl, a $10^{-4}$ mM ABA solution was poured into another Petri dish, and Arabidopsis plants pulled out from the MS plates were soaked in this solution, thereby exposing these Arabidopsis plants to ABA stress. Furthermore, another MS plate on which Arabidopsis plants were growing was placed in an incubator at 4° C., thereby exposing these Arabidopsis plants to low temperature stress.

Next, the Arabiodopsis plants exposed to the various stresses were homogenized under liquid nitrogen, and then total RNA was extracted (Nagy F, Kay S A and Chua N-H, 1988, Analysis of gene expression in transgenic plants. In Gelvin and Schilperoort, eds, Plant Molecular Biology Manual, B4. Kluwer Academic Publishers, Dordrecht, pp 1–29). The obtained RNA solution, 5 $\mu$g per lane, was subjected to electrophoresis using 1% agarose gel. Following electrophoresis, RNA was transferred from 1% agarose gel to nylon membrane (plus charge). The resultant nylon membrane was subjected to Northern blot analysis.

Probes used for Northern blot analysis were RNA probes that had been labeled with DIG using DIG RNA Labeling Kit (SP6/T7) (Roche) and using a plasmid obtained in 1 above as a template. Expression of AtGolS1 to 3 in response to various stresses can be confirmed by this Northern blot analysis.

Figure 2:
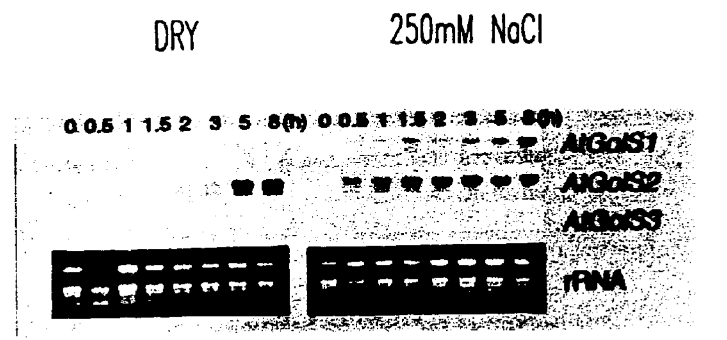
FIG. 2 is a photograph of electrophoresis by which expression of AtGo1S1 to 3 in Arabidopsis plants that grew on Petri dishes and were exposed to various stresses was confirmed.
Figure 2:
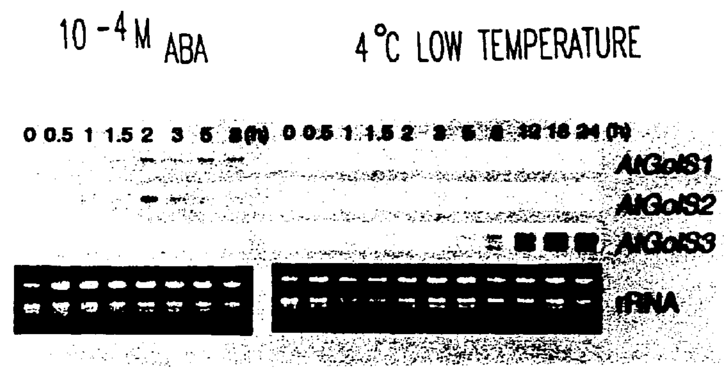
Figure 3A:
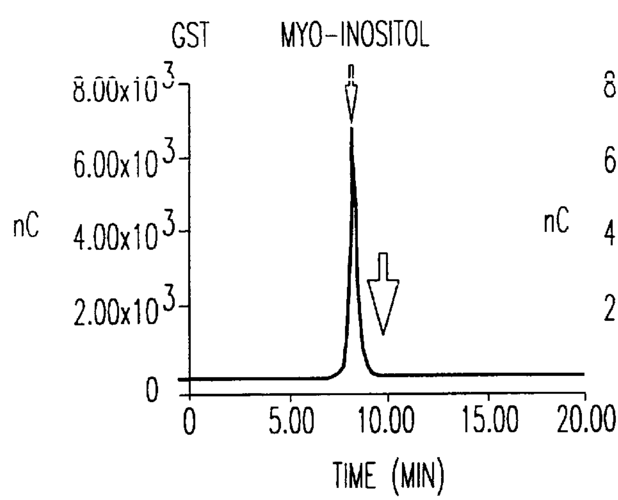
FIG. 3 includes characterization graphs showing the results of measuring galactinol synthetic activity in GST-AtGo1S1 protein, GST-AtGo1S2 protein, and GST-AtGo1S3 protein. Graph A is a case with GST alone, B is a case with GST-AtGo1S1 protein, C is a case with GST-AtGo1S2 protein, and D is a case with GST-AtGo1S3 protein.
Figure 3B:
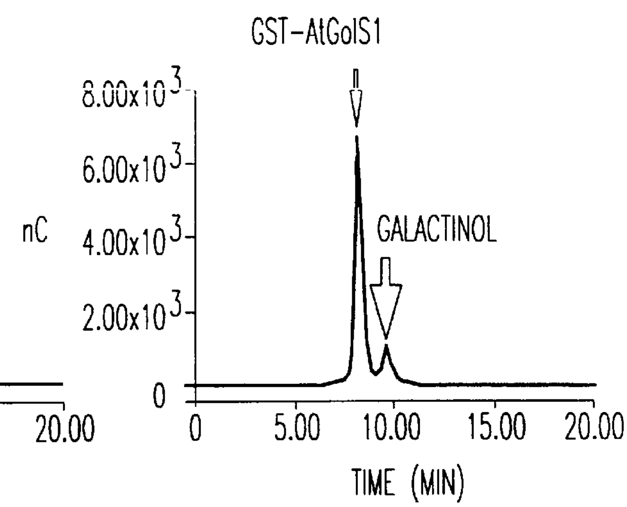
Figure 3C:
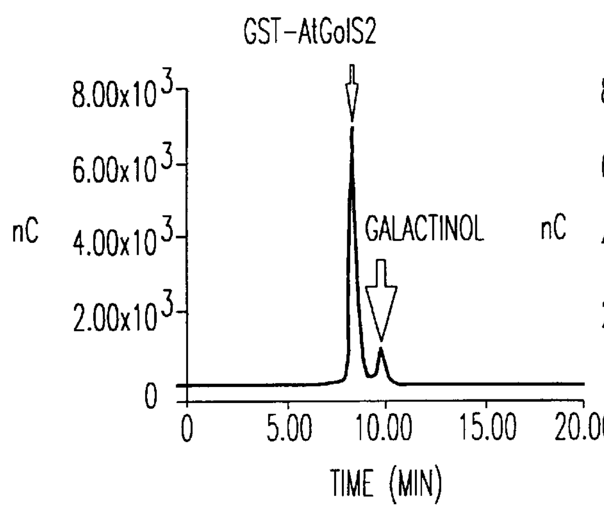
Figure 3D:
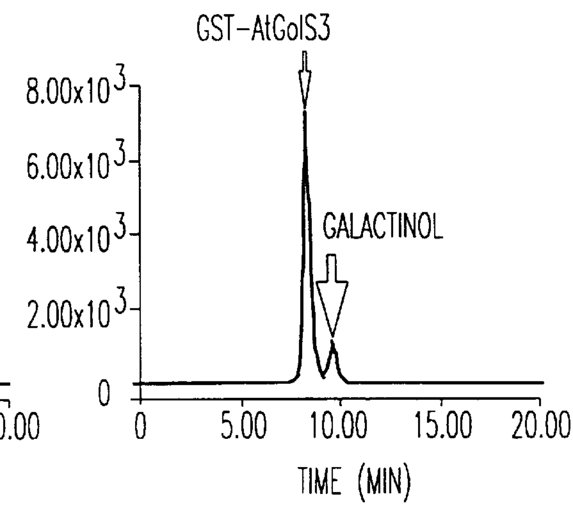

FIGS. 1 and 2 show the results. FIG. 1 shows a photograph of electrophoresis by which expression of AtGolS1 to 3 was confirmed in the Arapidopsis plants grown in soil. FIG. 2 shows a photograph of electrophoresis by which expression of AtGolS1 to 3 was confirmed in the Arapidopsis plants grown on a Petri dish. As shown in FIGS. 1 and 2, expression of AtGolS1 and AtGolS2 are induced in response to drought stress or to high salt concentration stress. Expression of AtGolS3 is induced in response to low temperature stress. In addition, expression of AtGolS1 and AtGolS2 is also induced in response to ABA stress.

3. Function of AtGolS1 to 3 Proteins

To confirm galactinol synthetic activity in AtGolS1 to 3 proteins, first, AtGolS1 to 3 proteins were purified. Coding regions in the full length cDNA as prepared in 1 above were isolated by PCR using the following primers.

```
Primer 7:
5'-CGCGGATCCATGGCTCCGGGGCTTACTCAAAC-3'
(SEQ ID NO:10)

Primer 8:
5'-CGCGGATCCCCACCGACAATTTTAACTCCTGG-3'
(SEQ ID NO:11)

Primer 9:
5'-CGCGGATCCATGGCACCTGAGATCAATACC-3'
(SEQ ID NO:12)

Primer 10:
5'-CGCGGATCCGAGGCGTATGCAGCAACGAGC-3'
(SEQ ID NO:13)

Primer 11:
5'-CGCGGATCCATGGCACCTGAGATGAACAACAAGTTG-3'
(SEQ ID NO:14)

Primer 12:
5'-CGCGGATCCCTGGTGTTGACAAGAACCTCGCTC-3'
(SEQ ID NO:15)
```

That is, using primers 7 and 8, the coding region of AtGolS1 protein was amplified; using primers 9 and 10, that of AtGolS2 protein was amplified; and using primers 11 and 12, that of AtGolS3 protein was amplified.

Next, the resulting DNA fragment was cloned into an EcoRV site of pBluescript II SK+ (Stratagene). Then whether any mutation had been introduced into DNA nucleotide sequence obtained by PCR was confirmed. A DNA fragment shown to have no mutation was cloned into BamHI site of pGEX4T-1 (Amersham Pharmacia biotech) containing a glutathione S-transferase (GST) gene so that the cloned insert was in the correct frame, thereby constructing chimera plasmids pGST-AtGolS1, pGST-AtGolS2, and pGST-AtGolS3. *E. coli* strain JM109 was transformed using these pGST-AtGolS1, pGST-AtGolS2, or pGST-AtGolS3 plasmids, and then cultured on LB media at 37° C.

When the OD600 of the culture solution reached about 0.5, isopropyl β-D-thiogalactoside (IPTG) was added to the solution, followed by culturing for another 12 hours at 17° C. *E. coli* was collected, washed, and then suspended in extraction buffer [10 mM Tris-HCl (pH 8.0), 5 mM MgCl, 5% glycerol, 0.1 mM phenylmethylsulfonyl fluoride (PMSF), and 0.1 mM dithiothreitol (DTT)]. GST fusion protein was purified by chromatography using glutathione-Sepharose 4B [the GST gene fusion system (Amersham Pharmacia biotech)], followed by thrombin cleavage of the GST portion. The concentration of the resultant protein was determined using a protein assay kit (Bio-Rad, CA, USA).

Galactinol synthetic activity of GST-AtGolS1 protein, GST-AtGo1S2 protein and GST-AtGolS3 protein was measured according to the methods as described in Liu, J. J. et al., Plant Physiol. 109: 505–511, 1995. That is, 0.017 mg of protein to be measured was added to a reaction buffer (50 mM Hepes-Na, 2 mM DTT, pH7.0) containing 4 mM $MnCl_2$, followed by incubation at 30° C. for 15 minutes.

Next, 4 mM UDP-galactose, 20 mM myo-inositol and 0.16 mg of BSA were added to the resulting solution, followed by another incubation at 30° C. for 30 minutes in a total 1 ml of a system for galactinol synthesis reaction to proceed. Following reaction, galactinol synthesis reaction was stopped by addition of 2 ml of cold 100% EtOH.

FIG. 3 (A to D) shows the results of measuring galactinol synthetic activity for each of GST-AtGolS1 protein, GST-AtGolS2 protein and GST-AtGolS3 protein. FIG. 3A is a result of a control experiment without the subject protein. As shown in FIG. 3 (B to D), GST-AtGolS1 protein, GST-AtGolS2 protein and GST-AtGolS3 protein each possesses galactinol synthetic activity.

4. Generation of Transgenic Plant

As clearly shown in 1 to 3 above, both AtGolS1 and AtGolS2 have galactinol synthetic activity and the expression of the two were induced in response to drought stress and high salt concentration stress. Accordingly, a transgenic plant excessively expressing AtGolS1 and AtGolS2 was generated. Specimens used herein were *Arabidopsis thaliana* (L.) Heynh. Ecotype Columbia. This Arabidopsis plant was sowed on a plastic pot with a diameter of 9 cm containing culture soil, grown for 6 weeks under light of 16 hours at 22° C., and then transformed as described below.

Figure 4:
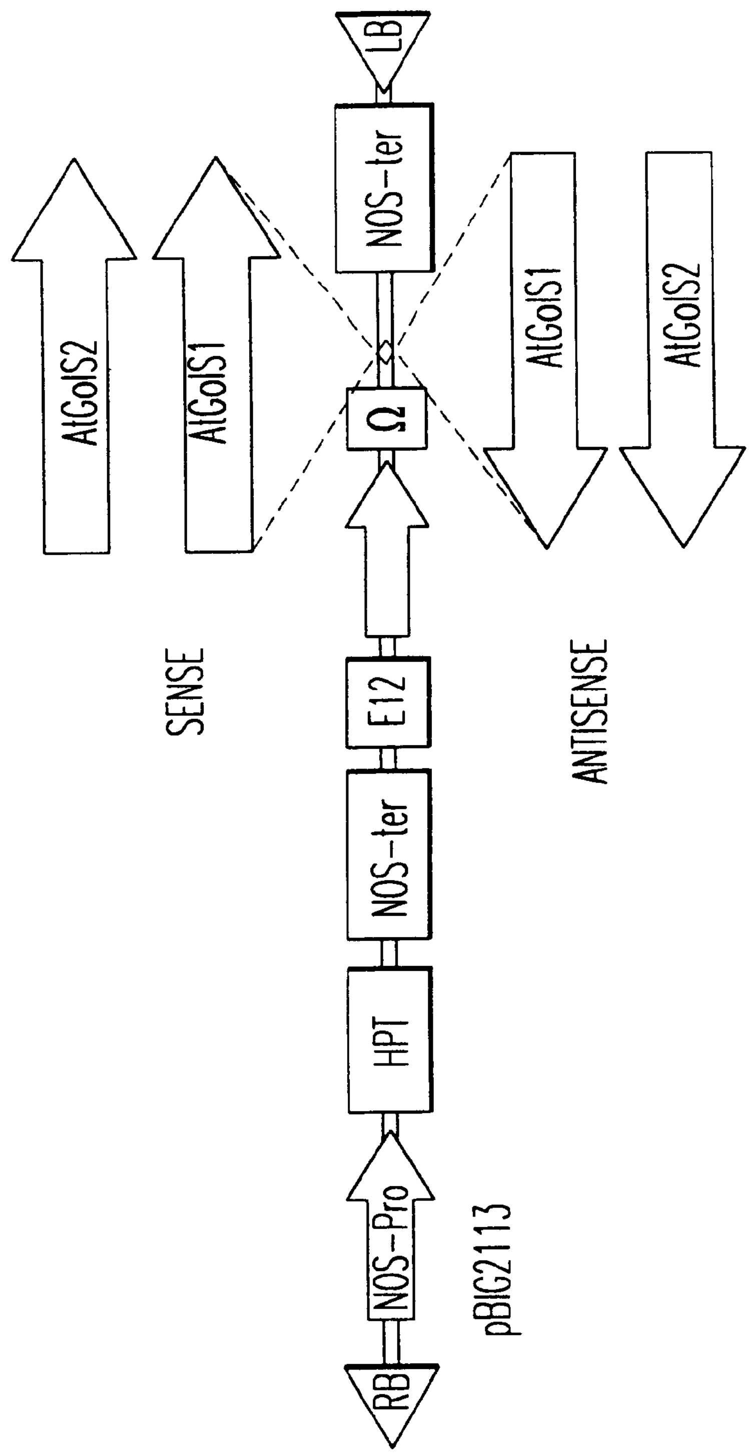
FIG. 4 is a schematic diagram showing the structures of vectors used for generating transgenic plants.

As shown in FIG. 4, a vector (pBE2114NOT) lacking a GUS reporter gene was constructed from a pBE2113 vector (Mitsuhara, I. et al. Plant Cell Physiol. 37: 49–59, 1996) having a kanamycin-resistant marker and a 35S promoter of cauliflower mosaic virus. Next, a vector (pBIG2113NOT) was constructed by substituting a kanamycin-resistant gene in pBE2114NOT with a hyglomycin-resistant gene. Finally, two vectors were constructed. That is, a vector containing cDNA of any one of AtGolS1 to 3 isolated from Arabidopsis into BamHI site in normal direction (sense); and a vector containing the same type of cDNA reversely integrated into BamHI site (antisense) were constructed.

Figure 5:
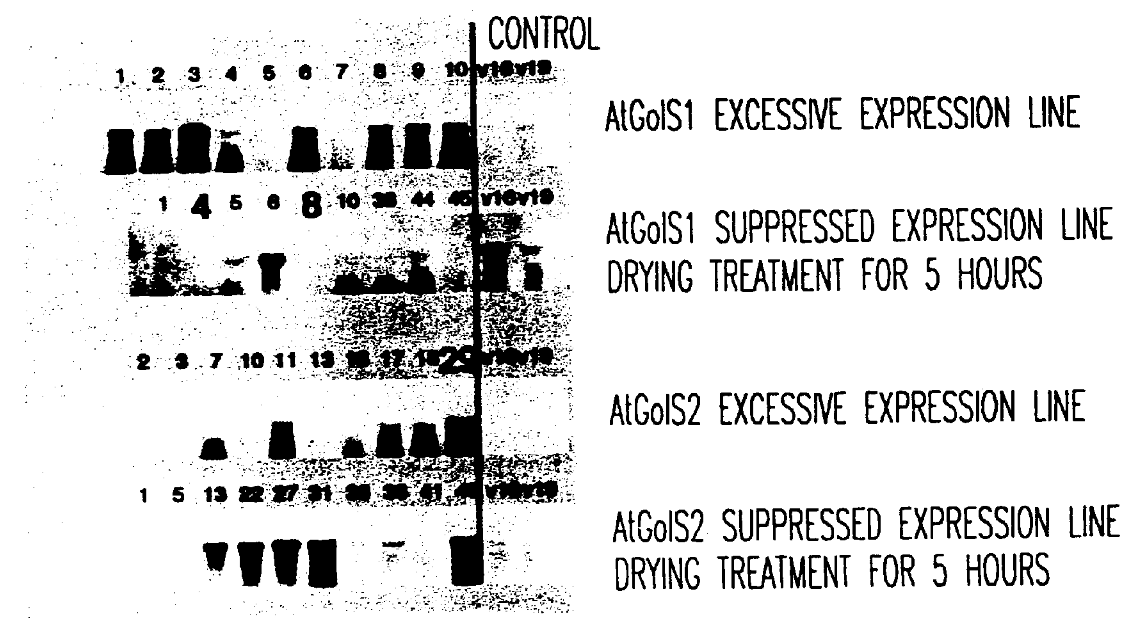
FIG. 5 is a photograph of electrophoresis showing the results of confirming the expression amount of the introduced genes in transgenic plants by Northern blot analysis.

The obtained vectors were introduced into soil bacteria (*Agrobacterium tumefaciens* strain GV3101 (pMP90)) by triparental mating. Soil bacteria containing the gene of interest were selected based on their resistance to kanamycin (Km). Then wild type Arabidopsis plants were infected with the selected bacteria by the infiltration method under reduced pressure (Bechtold, N. et al. C. R. Acad. Sci. Paris. LifeSci. 316, 1194–1199, 1993). Dry seeds were harvested from the infected plants, and then sowed and grown on agar plates supplemented with hyglomycin. Thus T1 transformants (first generation) were selected. Next, T2 transformant seeds harvested from the T1 transformants. The expression amount of the introduced genes in the resulting plants was confirmed. Transgenic plants showing sufficient expression of the introduced gene were used in the following experiments. That is, T2 transformants (second generation) seeds were sowed on MS plates supplemented with 10 $\mu$g/ml of hyglomycin, treated at 4° C. for 2 days, and then grown at 22° C. for 3 weeks. Plants containing the gene introduced in the sense direction were harvested untreated. Arabidopsis plants containing the gene of interest introduced in the antisense direction were gently pulled out of the MS plates, and then agar attached to the roots were gently removed with a kim wipe. Subsequently the plants were put into an empty Petri dish, and subjected to drying treatment with its cover closed for approximately 30 minutes to avoid rapid drying, thereby exposing the Arabidopsis plants to drought stress. Then, the plants were collected after 8 hours. Northern blot analysis was conducted using probes labeled with DIG prepared as described above so as to confirm the expression amount of the introduced gene. FIG. 5 shows the result. As shown in FIG. 5, No. 1 and No. 3 indicate excessive expression of AtGols1 gene when this gene was introduced. No. 1 and No. 3 were determined as transgenic plants. Similarly, No. 11 and No. 29 indicate excessive expression of AtGols2 when this gene was introduced. No. 11 and No. 29 plants were determined as transgenic plants.

In addition, FIG. 5 also shows the result of confirmation of each expression amount of AtGols1 gene and AtGols2 gene when these genes were introduced in the antisense direction. As shown in FIG. 5, No. 4 and No. 8 indicate suppressed expression of AtGo1s1 gene when this gene was introduced in the antisense direction. Moreover, No. 1 and No. 5 indicate suppressed expression of AtGols2 gene when AtGols2 gene was introduced in antisense direction.

No. 29 seeds containing AtGols2 gene introduced, Nos. 4 and 8 seeds containing AtGols1 gene introduced in the antisense direction, and seeds containing control vectors having only pBIG2113NOT were sowed on agar plates having nutrient salts as described above (Valvekens, D. et. al., Proc. Natl. Acad. Sci. USA 85, 5536–5540, 1988) and grown for 2 weeks. The resulting four types of plants were separately transplanted, four individual plants of the same type per pot, in plastic pots with a diameter of 9 mm containing soil (vermiculite:verlite=1:1). Then the plants were grown at 22° C. under light of 16 hours. Three weeks after sowing (1 week after transplantation), watering of the pots with the plants was stopped to expose the plants to drought stress. Photographs were taken on day 16 after watering had ceased. FIG. 6 shows the results.

As shown in FIG. 6, No. 29 transgenic plants excessively expressing AtGols2 gene were confirmed to possess drought resistance superior to the plants showing suppressed expression of AtGols1 gene and to the plants with control vectors. Moreover, the plants with control vectors and No. 29 plants were allowed to absorb water again on day 17 after that watering had ceased. FIG. 7 shows the photographs taken on day 5 after re-absorption of water. As clearly shown in FIG. 7, No. 29 plants grew even under conditions the plants containing control vectors, which had reabsorbed water on day 17 after watering had ceased, withered.

Figure 8:
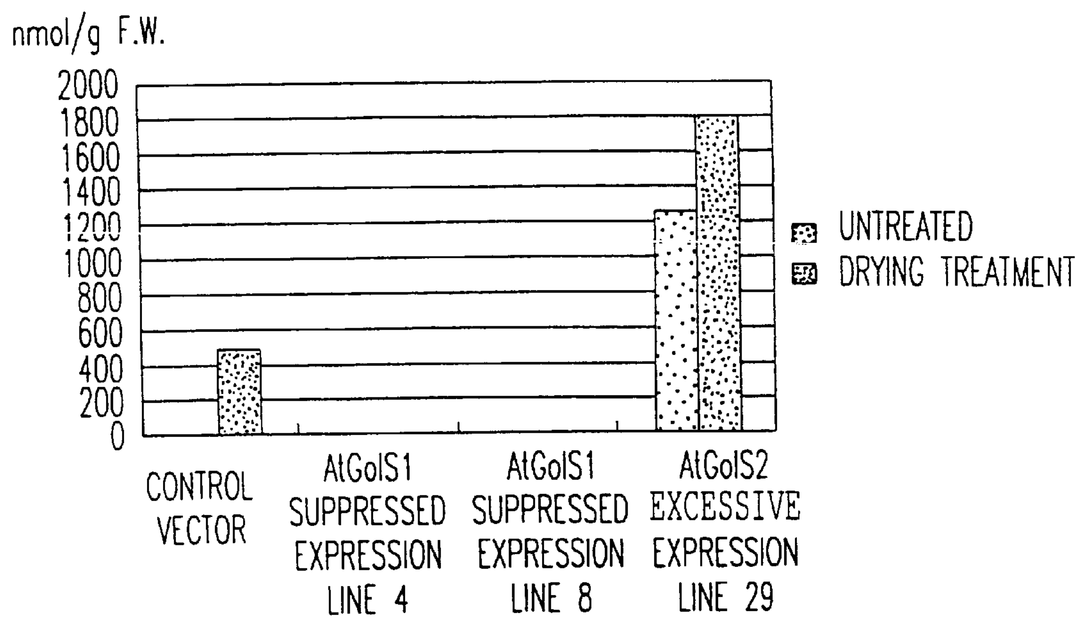
FIG. 8 is a characterization graph comparing galactinol contents in transgenic plants to each other.

On the other hands, FIG. 8 shows the results of measuring galactinol content in the plant bodies shown in FIG. 6. As shown in FIG. 8, galactinol content in No. 29 plant body increased significantly compared to that in the plant body showing suppressed expression of AtGols1 gene and to the plant body containing only the vector. That is, No. 29 plant body having good drought resistance accumulated in vivo a large amount of galactinol. These results reveal that in vivo accumulation of a large amount of galacitnol can increase good drought resistance to a plant.

Figure 9:
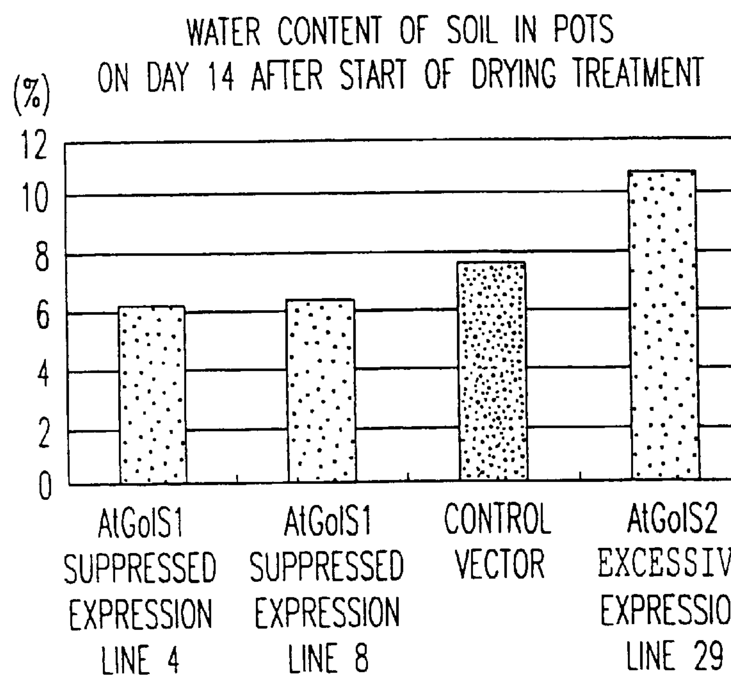
FIG. 9 is a characterization graph comparing water contents of soil, on which transgenic plants grew, to each other.
Figure 10:
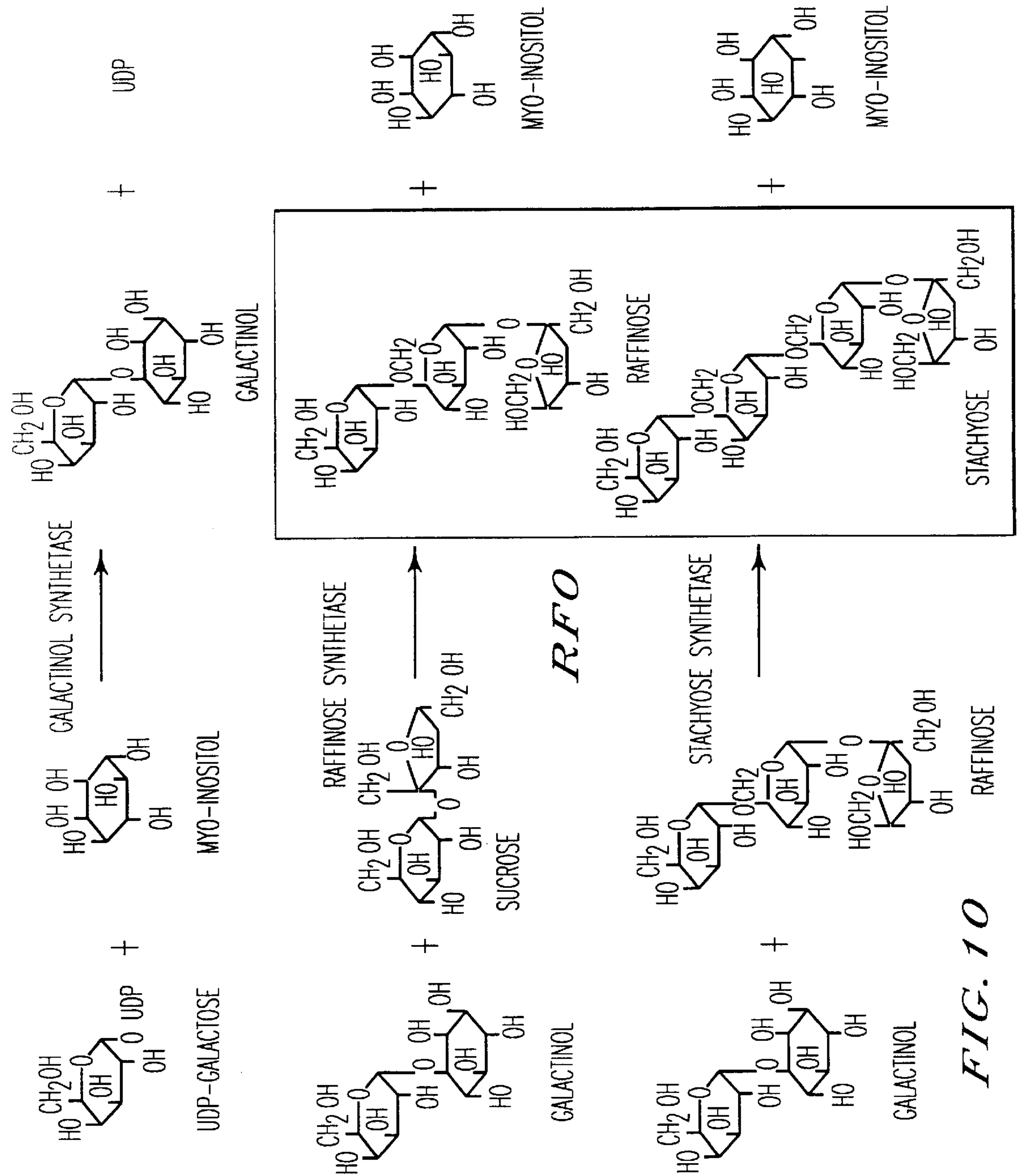
FIG. 10 is a schematic diagram showing the RF0 synthetic pathway.

Furthermore, FIG. 9 shows the results of measuring water content of soil filled in plastic pots for the plants shown in FIG. 6. As shown in FIG. 9, water content of soil for No. 29 plant body was higher than that for the plant body with only vectors and for the plant body showing suppressed expression of AtGols1 gene. These results strongly suggest that in a plant body a large amount of galactinol is accumulated, transpiration of water is suppressed by a mechanism, such as pore-closing control, or that the plant is provided with good drought resistance.

As described in detail above, according to the present invention, accumulation of a large amount of galactinol in a plant body can provide stress resistance for the plant. Therefore, the present invention enables production of a plant resistant to various environmental stresses.

SEQUENCE LISTING FREE TEXT

SEQ ID NOS: 4 to 15 are synthetic primers.

---

What is claimed is:

1. A method of increasing drought resistance of a plant, comprising introducing a polynucleotide encoding a protein comprising the amino acid sequence in SEQ ID NO:2 into the plant, wherein the protein is expressed in an amount sufficient to increase the drought resistance of the plant, wherein the drought resistance of the plant is higher compared to the plant prior to introducing the polynucleotide.

2. The method of claim 1, wherein the plant is selected from the group consisting of Arabidopsis, Glycine, Vicia, rape-seed, Helianthus, Gossypium, sugar beet, Oryza, Saccharum, corn, and Sorghum.

3. The method of claim 1, wherein the polynucleotide is introduced into the plant on a vector.

4. The method of claim 1, wherein the polynucleotide is introduced into a chromosome of the plant.

5. A method of increasing the salt tolerance of a plant, comprising introducing a polynucleotide encoding a protein comprising the amino acid sequence in SEQ ID NO:2 into the plant, wherein the protein is expressed in an amount sufficient to increase salt tolerance of the plant, wherein the salt tolerance of the plant is higher compared to the plant prior to introducing the polynucleotide.

6. The method of claim 5, wherein the plant is selected from the group consisting of Arabidopsis, Glycine, Vicia, rape-seed, Helianthus, Gossypium, sugar beet, Oryza, Saccharum, corn, and Sorghum.

7. The method of claim 5, wherein the polynucleotide is introduced into the plant on a vector.

8. The method of claim 5, wherein the polynucleotide is introduced into a chromosome of the plant.

* * * * *